(12) United States Patent
Leyden et al.

(10) Patent No.: US 7,670,341 B2
(45) Date of Patent: Mar. 2, 2010

(54) ORTHOPAEDIC DEVICE WITH LOCKING BARREL

(75) Inventors: Matthew V. Leyden, St. Paul, MN (US); William Thomas Ryder, Victoria, MN (US); Wesley D. Johnson, Eden Prairie, MN (US); Aaron J. Bisek, Elk River, MN (US); Marc E. Ruhling, Goshen, IN (US); Matthew S. Wallace, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 810 days.

(21) Appl. No.: 11/303,833

(22) Filed: Dec. 16, 2005

(65) Prior Publication Data

US 2007/0162011 A1 Jul. 12, 2007

(51) Int. Cl.
 *A61B 17/56* (2006.01)
(52) U.S. Cl. .......................... 606/65; 606/280; 606/71; 606/281
(58) Field of Classification Search .................... 606/65, 606/66, 67, 68, 280, 70, 71, 281, 282, 283, 606/284, 285, 286, 287, 288, 289, 290, 291, 606/292, 293, 294, 295, 296, 297, 298, 299; 403/109.1, 109.2, 109.3, 109.4, 109.5, 109.6, 403/109.7, 109.8
See application file for complete search history.

(56) References Cited

U.S. PATENT DOCUMENTS

| | | | |
|---|---|---|---|
| 2,526,959 A | 10/1950 | Lorenzo | |
| 3,554,193 A | 1/1971 | Konstantinou | |
| 3,996,931 A | 12/1976 | Callender, Jr. | |
| 4,079,965 A * | 3/1978 | Moughty et al. | 285/7 |
| 4,095,591 A | 6/1978 | Graham, Jr. et al. | |
| 4,172,452 A | 10/1979 | Forte et al. | |
| 4,432,358 A | 2/1984 | Fixel | |
| 4,438,762 A * | 3/1984 | Kyle | 606/65 |
| 4,465,065 A | 8/1984 | Gotfried | |
| 4,530,355 A | 7/1985 | Griggs | |

(Continued)

FOREIGN PATENT DOCUMENTS

DE 198 20 015 12/1999

(Continued)

*Primary Examiner*—Eduardo C Robert
*Assistant Examiner*—Jan Christopher Merene
(74) *Attorney, Agent, or Firm*—Maginot, Moore & Beck

(57) ABSTRACT

A bone fixation assembly includes a side plate for mounting on a bone and a barrel for receiving a portion of a lag screw, and configured to be inserted into a hole in the side plate. A mechanical spring located at the upper portion of the barrel biases a first detent portion toward a locking position with a second detent portion located on the side plate such that rotation of the barrel within the hole from a first position to a second position causes a compressing portion on the detent portion to contact a compressing portion on the second detent portion thereby compressing the mechanical spring so as to allow the barrel to be rotated to a third position wherein the mechanical spring is allowed to bias the first detent portion into the locking position such that a retaining portion of the first detent is adjacent to a retaining portion of the second detent and rotation of the barrel with respect to the side plate is restricted.

19 Claims, 8 Drawing Sheets

U.S. PATENT DOCUMENTS

| | | | |
|---|---|---|---|
| 4,612,920 A | | 9/1986 | Lower |
| 4,616,638 A | | 10/1986 | Griggs |
| 4,617,922 A | | 10/1986 | Griggs |
| 4,621,629 A | | 11/1986 | Koeneman |
| 4,657,001 A | * | 4/1987 | Fixel .......................... 606/66 |
| 4,759,352 A | | 7/1988 | Lozier |
| 4,794,919 A | | 1/1989 | Nilsson |
| 5,087,260 A | * | 2/1992 | Fixel .......................... 606/65 |
| 5,324,292 A | | 6/1994 | Meyers |
| 5,429,641 A | | 7/1995 | Gotfried |
| 5,514,138 A | * | 5/1996 | McCarthy ................... 606/65 |
| 5,658,339 A | | 8/1997 | Tronzo et al. |
| 5,749,872 A | | 5/1998 | Kyle et al. |
| 5,957,927 A | | 9/1999 | Magee et al. |
| 6,007,536 A | | 12/1999 | Yue |
| 6,183,474 B1 | | 2/2001 | Bramlet et al. |
| 6,533,789 B1 | * | 3/2003 | Hall, IV et al. ............. 606/281 |
| 6,623,486 B1 | | 9/2003 | Weaver et al. |
| 6,645,209 B2 | | 11/2003 | Hall, IV et al. |
| 7,135,023 B2 | * | 11/2006 | Watkins et al. ................ 606/65 |
| 2004/0254579 A1 | * | 12/2004 | Buhren et al. ................. 606/71 |
| 2005/0010224 A1 | * | 1/2005 | Watkins et al. ................ 606/65 |
| 2005/0234457 A1 | * | 10/2005 | James et al. .................. 606/69 |
| 2006/0241606 A1 | * | 10/2006 | Vachtenberg et al. ......... 606/65 |
| 2008/0119855 A1 | * | 5/2008 | Hoegerle et al. .............. 606/65 |

FOREIGN PATENT DOCUMENTS

| | | |
|---|---|---|
| EP | 0 468 195 | 6/1991 |
| WO | 2004/075766 | 9/2004 |
| WO | WO 2004/082493 | 9/2004 |
| WO | WO 2004/100809 | 11/2004 |
| WO | WO 2004/110292 | 12/2004 |

* cited by examiner

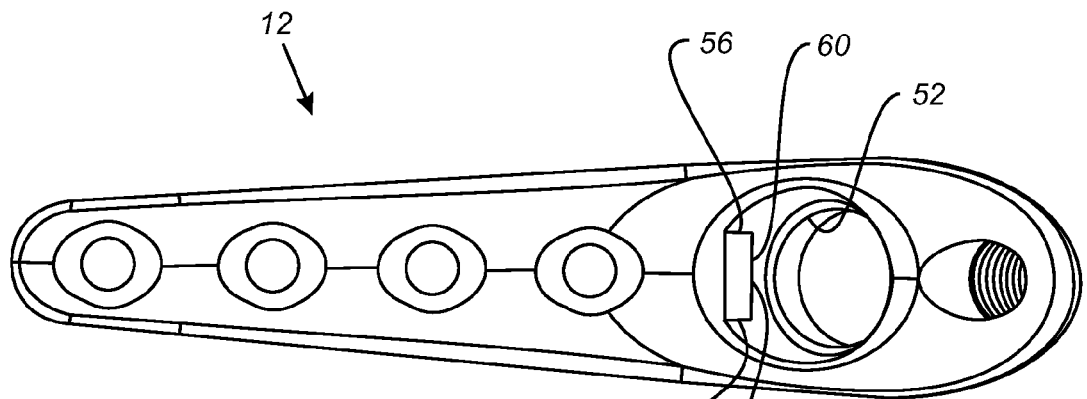
Fig. 4
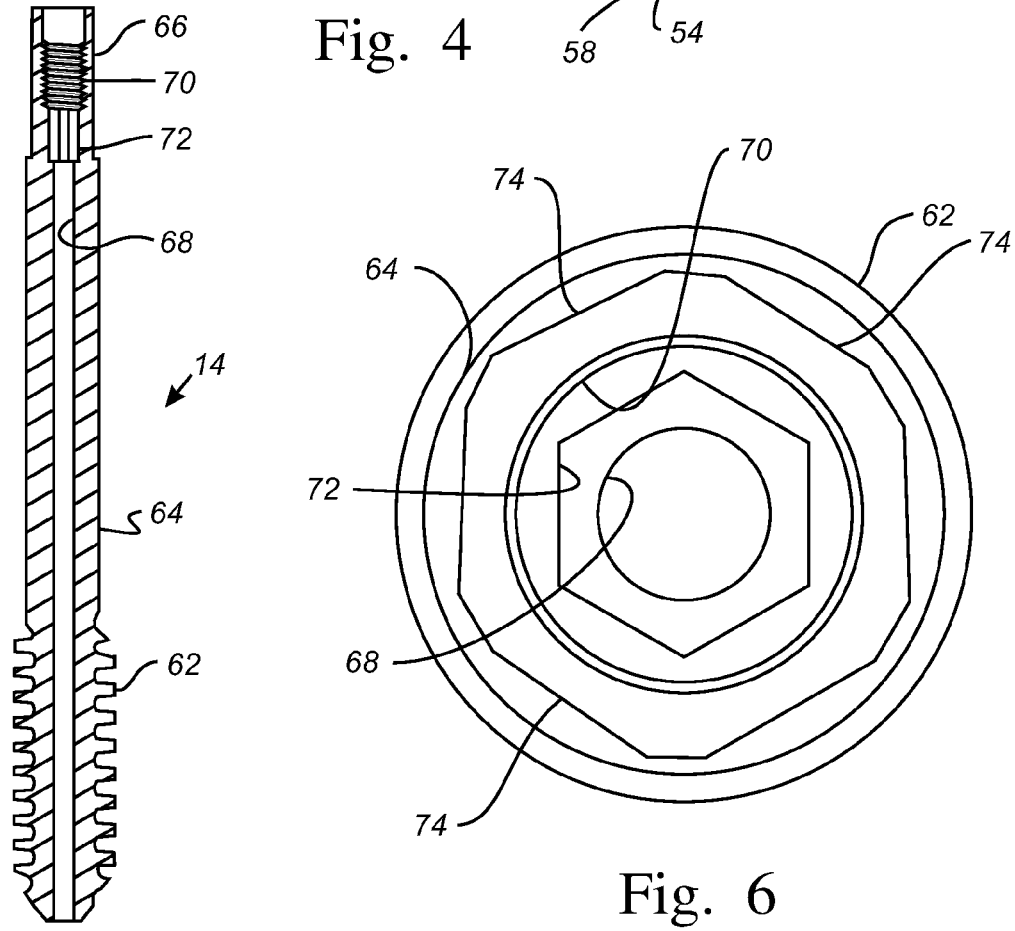
Fig. 5
Fig. 6

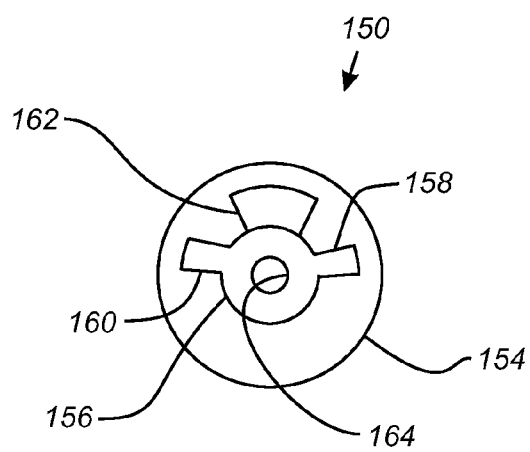
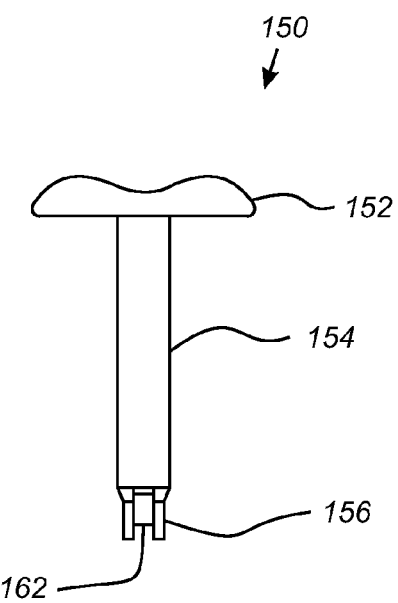
Fig. 22
Fig. 23

ORTHOPAEDIC DEVICE WITH LOCKING BARREL

FIELD OF THE INVENTION

This invention relates to orthopedic appliances and, more particularly, to devices used in the treatment of hip fractures in which the femur is the site of the fracture.

BACKGROUND

Hip fractures, wherein the femur is fractured one or more times in the area of the intertrochanteric region of the femur, or immediately subjacent the head, are fairly common. A great many devices have been proposed for the reduction of fractures of this type. While many of these devices have found application and have advantages relative one to another, there remain some problems and areas of continuing concern.

Such reduction devices consist, basically, of an elongate lag screw which is threaded on one end to be threadably received in the head of the femur, and is secured to a plate such that when the lag screw is tightened, the head of the femur is forcibly compressed at the fracture line to the remainder of the femur. Devices of this type, generally, are described in U.S. Pat. Nos. 2,526,959 and 3,554,193.

It has also been recognized that various adjustment features are important in treating certain femoral fractures. In general, fastener devices with such adjustment features employ a guide sleeve which is imbedded in one bone segment, such as the upper segment of the femur, in order to receive and adjustably hold one end of an axially elongated shaft, e.g. a lag screw, which extends through both fractured bone segments, with the end of the shaft opposite the guide sleeve being provided with structure for securing the shaft to the head of the femur. Because of absorption occurring during the healing process, it has been necessary, in some instances, to accommodate a certain amount of telescoping movement between the shaft and the guide sleeve. Clasping devices within this class generally are described in the U.S. Pat. Nos. 3,996,931 and 4,095,591.

Functionally, some of these devices perform quite satisfactorily for many fractures of the femur but limit the sequence in which the components may be implanted thereby limiting the flexibility of a surgeon. Moreover, with some devices used to angularly lock the lag screw, locking is achieved by torquing two components together. In these systems, special instruments may be needed to ensure application of the proper amount of torque to achieve the desired angular lock.

What is needed, therefore, is a bone fixation assembly that that allows for different sequencing of component implantation.

What is further needed is a bone fixation assembly that allows a lag screw to be angularly locked to a side plate in a plate first implantation as well as a lag screw first implantation.

What is also needed is a bone fixation assembly that provides a reliable indication of achieving an angular lock between a lag screw and a bone plate.

What is needed is a bone fixation assembly that maintains a reliable angular lock between a lag screw and a bone plate.

SUMMARY

A bone fixation assembly and method is disclosed. In one embodiment, the bone fixation assembly includes a side plate configured to be mounted on a bone and having a first detent portion, and hole therethrough. A barrel is insertable into the hole and has a bore for placement of a portion of lag screw. The assembly includes a mechanical spring for biasing a second detent portion into a locking position with the first detent portion so as to angularly lock the barrel in relation to the side plate.

In accordance with one method according to the invention, a side plate having a hole therethrough is mounted on a bone and a barrel is inserted into the hole. The barrel is angularly locked in relation to the side plate using a mechanical spring.

In a further embodiment, a bone fixation assembly includes a side plate for mounting on a bone, the side plate having a hole therethrough. The assembly further includes a barrel for receiving a portion of a lag screw that is configured to be inserted into the hole, the barrel including an upper portion and a lower portion. A mechanical spring located at the upper portion of the barrel is operable to bias a first detent portion including at least a first compressing portion and at least a first retaining portion toward a locking position with a second detent portion located on the side plate and including at least a second compressing portion and at least a second retaining portion. In this embodiment, rotation of the barrel within the hole from a first position to a second position causes the first compressing portion to contact the second compressing portion thereby compressing the mechanical spring so as to allow the barrel to be rotated to a third position wherein the mechanical spring is allowed to bias the first detent portion into the locking position such that the first retaining portion is adjacent to the second retaining portion and rotation of the barrel with respect to the side plate is restricted.

The above-described features and advantages, as well as others, will become more readily apparent to those of ordinary skill in the art by reference to the following detailed description and accompanying drawings.

BRIEF DESCRIPTION OF THE DRAWINGS

FIG. 4 depicts a top plan view of the bone plate of the bone fixation assembly of FIG. 1;

FIG. 5 depicts a cross-sectional view of the lag screw of the bone fixation assembly of FIG. 1;

FIG. 6 depicts a top plan view of the lag screw of the bone fixation assembly of FIG. 1;

FIG. 22 depicts a bottom elevational view of a tool that may be used to rotate the barrel of FIG. 1 in accordance with principles of the present invention;

FIG. 23 depicts a side elevational view of a tool that may be used to rotate the barrel of FIG. 1 in accordance with principles of the present invention;

DETAILED DESCRIPTION

Figure 1:
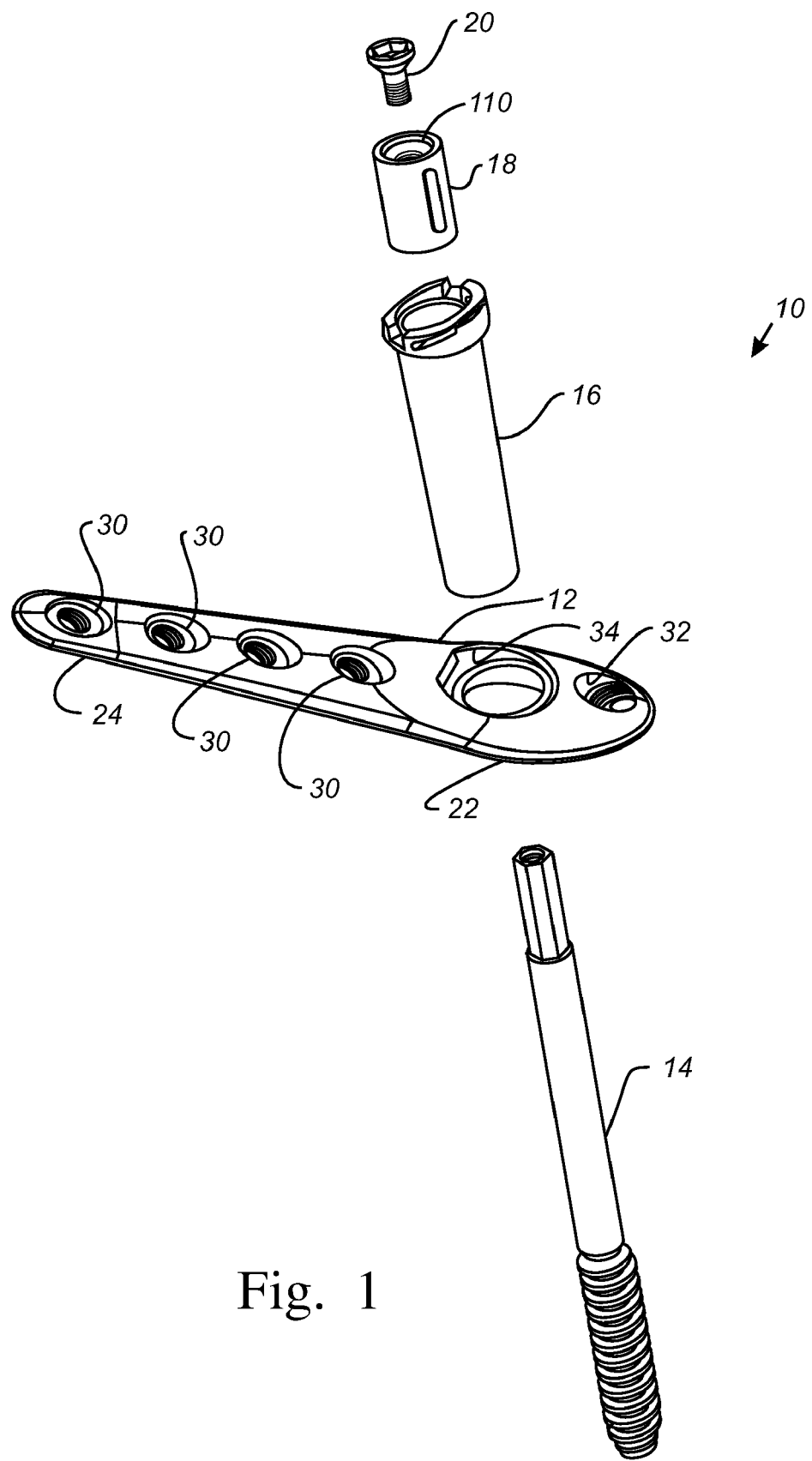
FIG. 1 depicts an exploded perspective view of a bone fixation assembly made in accordance with principles of the present invention.

FIG. 1 shows a bone fixation assembly 10 configured for use on the proximal end of a femoral bone. The bone fixation assembly 10 includes a side plate 12, a lag screw 14, a barrel 16, a sleeve 18 and a lag screw retainer 20. The components of the bone fixation assembly 10 are preferably constructed of titanium or another material acceptable for implantation.

Figure 2:
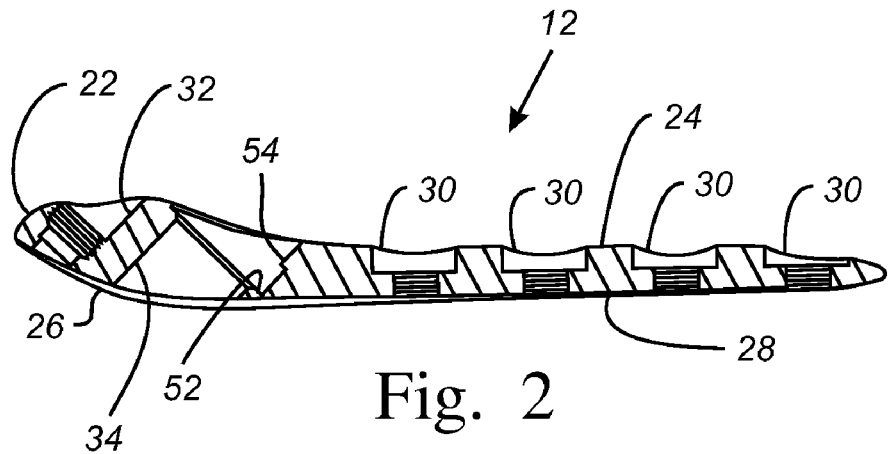
FIG. 2 depicts a side cross-sectional view of the bone plate of the bone fixation assembly of FIG. 1.
Figure 3:
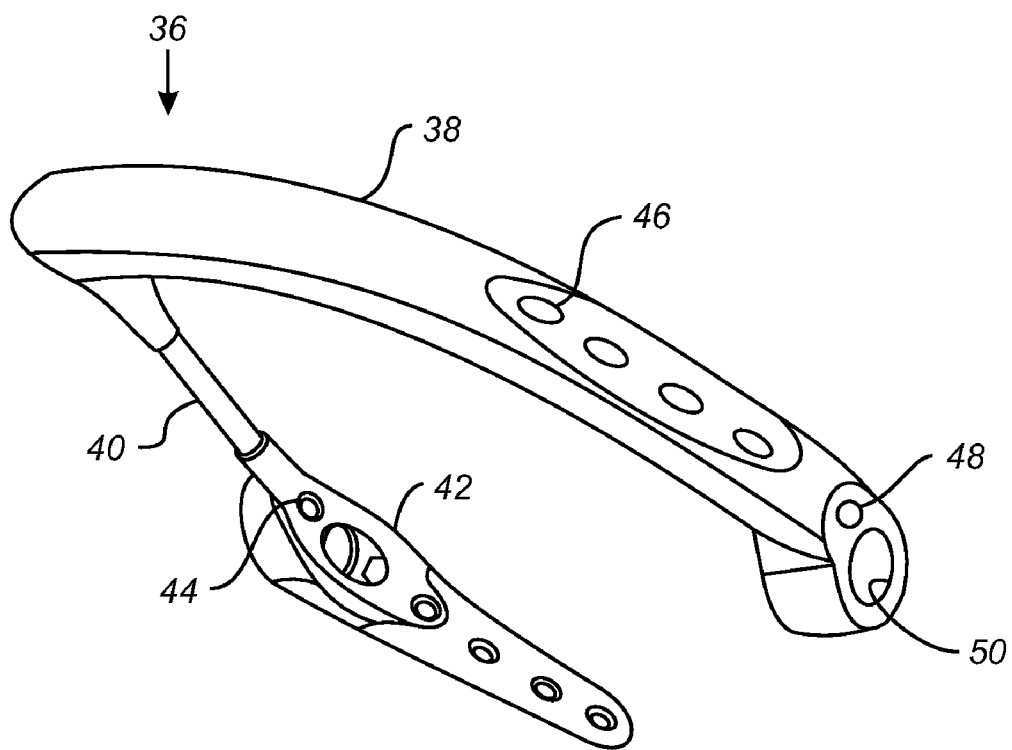
FIG. 3 depicts a top perspective view of a guide attached to the bone plate of the bone fixation assembly of FIG. 1 in accordance with principles of the present invention.

The side plate 12 includes a head portion 22 and a stem portion 24. As shown in FIG. 2, the inner side 26 of the head portion 22 curves upwardly away from the axis of the stem portion 24 to conform to the shape of the metaphysis of a bone. The inner side 28 of the stem portion 24 is configured to conform to the diaphysis of a bone. To this end, the inner side 28 of the stem portion 24 may be curved to generally conform to the curvature of a bone. A plurality of threaded holes 30 are located in the shaft portion 24. A threaded hole 32 and an unthreaded hole 34 are located in the head portion 22. The threaded holes 30 and 32 may be used to mount the side plate 12 onto a bone. The threaded hole 32 may further be used to mount a guide onto the side plate 12 as shown in FIG. 3 for positioning the side plate 12 onto a bone.

The guide 36 includes a handle 38, a stem 40 and a shoe 42. The shoe 42 is configured to receive the head portion 22 of the side plate 12 and includes a hole 44 that aligns with the threaded hole 32 of the side plate 12 for coupling of the guide 36 to the side plate 12. The handle includes a plurality of holes 46, a hole 48 and a hole 50. The holes 46 are configured to be aligned with the threaded holes 30 when the guide 36 is coupled to the side plate 12. The holes 46 thus provide a guide for insertion of screws or other devices through the threaded holes 30 even if the threaded holes 30 are not visible. Similarly, the holes 48 and 50 are configured to align with the threaded hole 32 and the unthreaded hole 34, respectively.

As seen most clearly in FIGS. 2 and 4, the unthreaded hole 34 includes an internal ledge 52 and a detent portion 54. The detent portion 54 is a ramp-like protrusion that extends into the unthreaded hole 34. The detent portion 54 includes two compressing portions 56 and 58 and a retaining portion 60. The hole 34 at the inner side 26 of the ledge 52 is configured to be of sufficient diameter to allow the lag screw 14 to pass through.

The lag screw 14, shown in FIG. 5, includes a threaded portion 62, a shaft 64, an upper portion 66 and an internal bore 68. The upper portion 66 includes an internally threaded section 70 and an internally faceted section 72. As shown in FIG. 6, which is a top elevational view, the lag screw 14 is widest at the threaded portion 62 and the upper portion 66 includes external facets 74. As previously stated, the threaded portion 62 is sized to pass completely through the hole 34. The threaded portion 62 is further sized such that the threaded portion 62 may not pass through the barrel 16.

Figure 7:
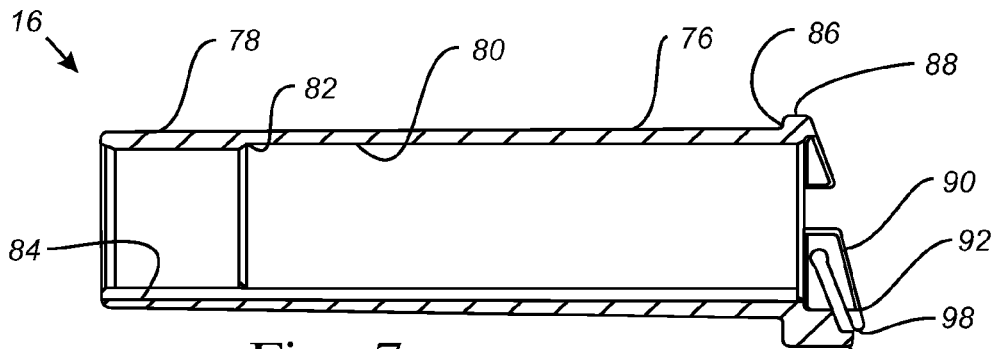
FIG. 7 depicts a cross-sectional view of the barrel of the bone fixation assembly of FIG. 1.
Figure 8:
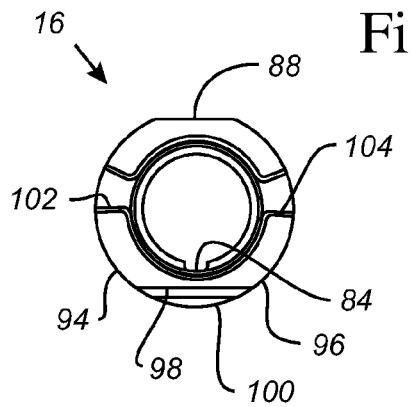
FIG. 8 depicts a top plan view of the barrel of the bone fixation assembly of FIG. 1.

The barrel 16 includes an upper portion 76, a lower portion 78 and an internal bore 80 shown in FIG. 7. A ledge 82 is located within the bore 80 toward the lower portion 78 of the barrel 16. A slot 84, also shown in FIG. 8, extends along the bore 80 from the upper portion 76 to the lower portion 78. An external ledge 86 circumscribes the upper portion 76 and a key 88 is formed in the external ledge 86. A mechanical spring 90 is located on the upper portion 76 and extends to a detent portion 92. The detent portion 92 includes two compressing portions 94 and 96 and a retaining portion 98. The upper portion 76 further includes a lip 100 and two torque slots 102 and 104.

Figure 9:
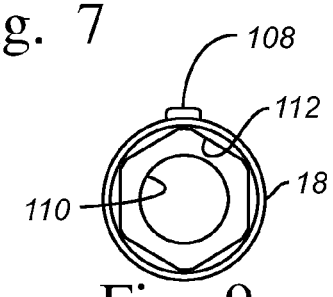
FIG. 9 depicts a top plan view of the sleeve of the bone fixation assembly of FIG. 1.
Figure 10:
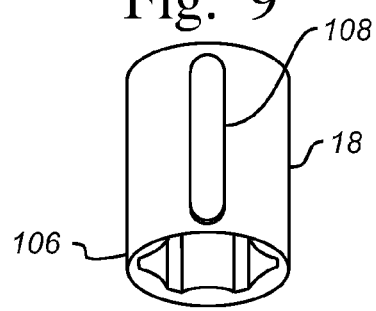
FIG. 10 depicts a perspective view of the sleeve of the bone fixation assembly of FIG. 1 showing a locking key and internal facets.

The sleeve 18, shown in FIGS. 9 and 10, is configured to fit within the bore 80 at the upper portion 76 of the barrel 16. More specifically, the diameter of the sleeve 18 is slightly less than the diameter of the bore 80 above the ledge 82. The sleeve 18 also includes a key 108 that is complimentarily formed to fit the slot 84. The combined diameter of the sleeve 18 and the key 108 is greater than the nominal diameter of the bore 80 at the upper portion 76 of the barrel 80. Thus, when the key 108 is aligned with the slot 84, the sleeve 18 may be inserted into the bore 80 at the upper portion 76 of the barrel 16. The sleeve 18 further includes an internally threaded portion 110 shown most clearly in FIG. 1, and an internally faceted portion 112.

Insertion of the sleeve 18 within the bore 80 angularly locks the sleeve 18 and the barrel 16 because the difference in the diameter between the bore 80 in the upper portion 76 of the barrel 16 and the diameter of the sleeve 18 is less than the thickness of the key 108. Accordingly, the key 108 is maintained within the slot 84 and the sleeve 18 cannot rotate within the barrel 16. Additionally, the diameter of the sleeve 18 is selected so as to be greater than the diameter of the bore 80 at the inner ledge 82. Thus, once inserted into the barrel 16, the sleeve 18 is maintained within the upper portion 76 of the barrel 16.

Figure 11:
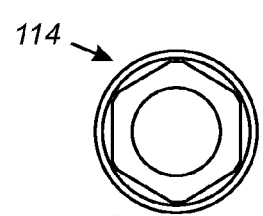
FIG. 11 depicts a top plan view of an alternative sleeve that may be used with the bone fixation assembly of FIG. 1 in accordance with principles of the present invention.
Figure 12:
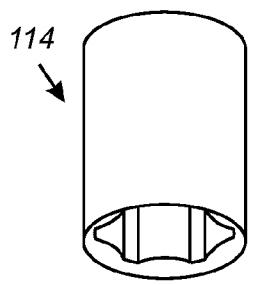
FIG. 12 depicts a perspective view of the alternative sleeve of FIG. 11.

An alternative embodiment of a sleeve is shown in FIGS. 11 and 12. The sleeve 114 is identical to the sleeve 18 with the exception that the sleeve 114 does not have a key. Therefore, the sleeve 114 is free to rotate within the bore 80. In this alternative embodiment, the diameter of the sleeve 114 is larger than the diameter of the bore 80 within the lower portion 78 of the barrel 16. Therefore, once inserted into the barrel 16, the sleeve 114 cannot pass through the barrel 16.

Figure 13:
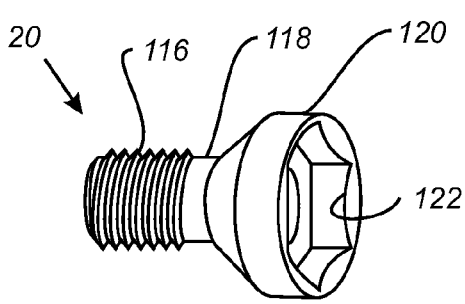
FIG. 13 depicts a perspective view of the lag screw retainer of the bone fixation assembly of FIG. 1.
Figure 14:
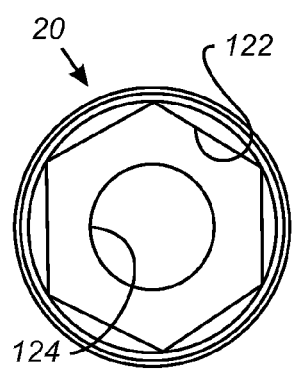
FIG. 14 depicts a top plan view of the lag screw retainer of the bone fixation assembly of FIG. 1.

FIGS. 13 and 14 depict the lag screw retainer 20. The retainer 20 includes a threaded portion 116, a neck portion 118 and a head portion 120. The retainer 20 further includes an internally faceted portion 122 and a bore 124.

Figure 15:
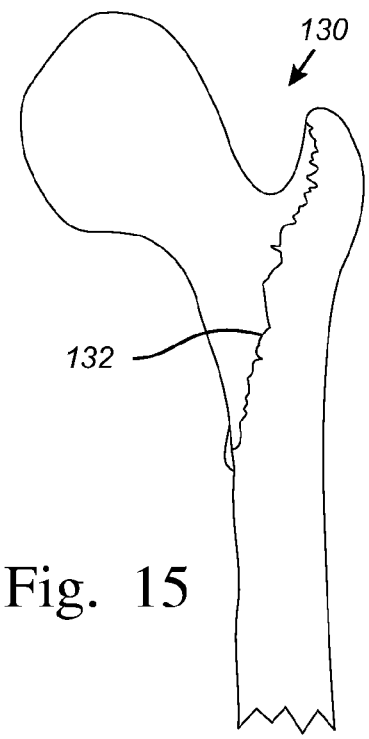
FIG. 15 depicts a femur with a fracture across the intertrochanteric region of the femur.
Figure 16:
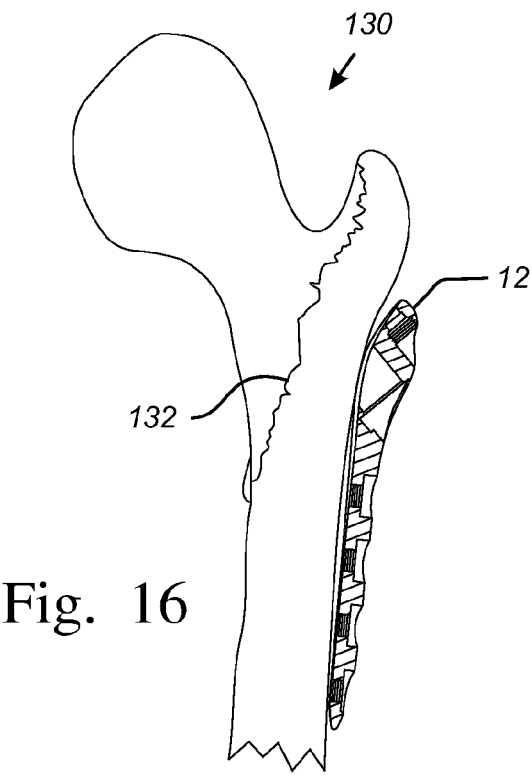
FIG. 16 depicts the placement of the side plate of FIG. 1 on the femur of FIG. 15 in accordance with aspects of one method of the present invention.

The components described above may be assembled in a number of alternative methods in accordance with the principles of the present invention. Aspects of one such method are discussed with reference to the femur 130 with a fracture 132 shown in FIG. 15. After preparation of the site in accordance with an acceptable procedure, the side plate 12 is mounted to the femur 130 as shown in FIG. 16. The side plate 12 may be positioned using a guide such as the guide 36 shown in FIG. 3. Additionally, other devices such as guide wires may be used as is known in the art to position the side plate 12 on the femur 130 at the desired location. The side plate 12 is then attached to the femur 130 by inserting screws (not shown) through the threaded holes 30. The femur 130 is then prepared for receiving the lag screw 14 and the lag screw 14 is inserted through the hole 34 and positioned within the femur 130.

Figure 17:
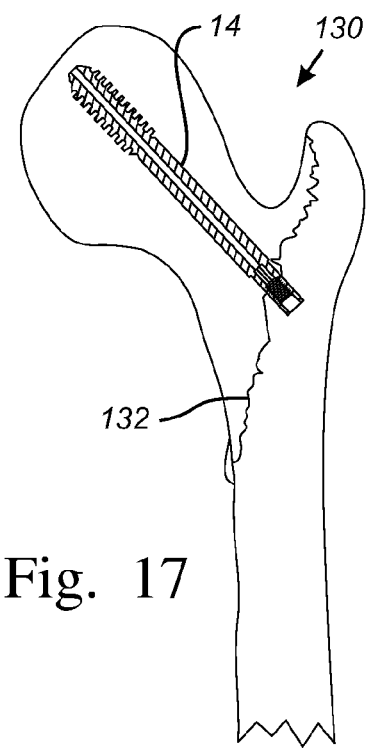
FIG. 17 depicts the placement of the lag screw of FIG. 1 with the shaft of the lag screw traversing the fracture of FIG. 15 in accordance with aspects of an alternative method of the present invention.

In an alternative approach, the lag screw 14 may be installed prior to installation of the side plate 12 as shown in FIG. 17. The preparation of the bone for insertion of the lag screw 14 is well understood by those of ordinary skill in the art, as are various techniques which may be used to guide the placement of the lag screw 14. Thereafter, the side plate 12 is positioned on the femur 130 is a manner similar to that set forth above.

Figure 18:
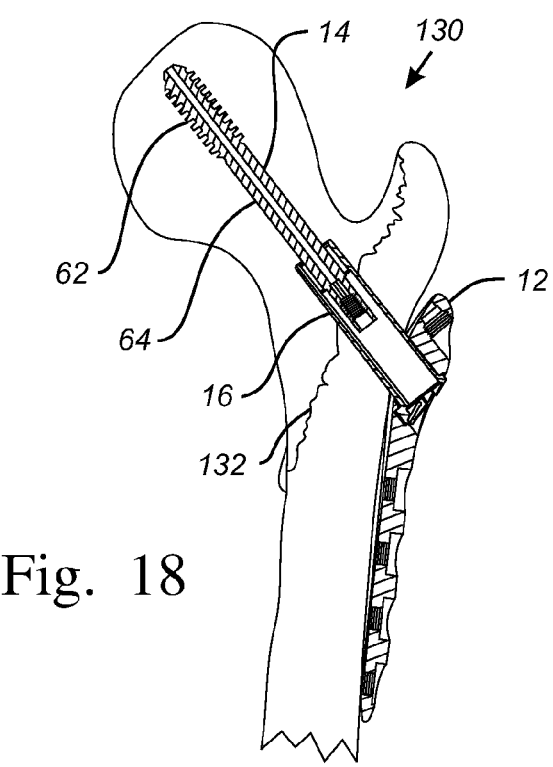
FIG. 18 depicts both the lag screw of FIG. 1 and the side plate of FIG. 1 on the femur of FIG. 15.

In either approach, the other component, i.e. the lag screw 14 or the side plate 12 may then be implanted along with the barrel 16 resulting in the configuration of FIG. 18. As shown in FIG. 18, the shaft 64 of the lag screw 14 and, because of the location of the fracture 132, the barrel 16 extend across the fracture 132. In this configuration, the threaded portion 62 is implanted in the portion of the fractured femur 130 farthest away from the side plate 12 and the upper portion 76 is located in the portion of the femur 130 on which the side plate 12 is mounted.

Figure 19:
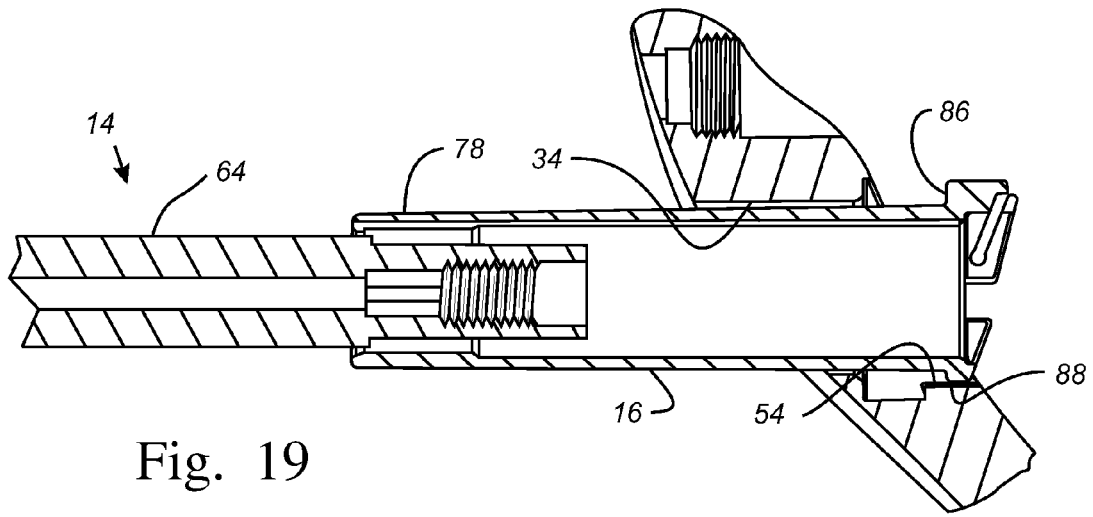
FIG. 19 depicts the barrel of the bone fixation assembly of FIG. 1 partially inserted within the side plate of FIG. 1 and around the lag screw of FIG. 1.

Insertion of the barrel 16 into the hole 34 is accomplished by aligning the key 88 with the detent portion 54 in the hole 34. Alignment of the key 88 with the detent portion 54, as shown in FIG. 19, allows the external ledge 86 to slide past the detent portion 54. As the barrel 16 is inserted into the hole 34, the lower portion 78 of the barrel 16 moves past the upper portion 66 of the lag screw 14 and a portion of the shaft 64. In an approach wherein the lag screw 14 is not fully inserted into the femur 130, movement of the barrel into the hole 34 may be restricted by the location of the threaded portion 62 since the threaded portion 62 has a larger diameter than the internal bore 80 in the lower portion 78 of the barrel 16.

Figure 20:
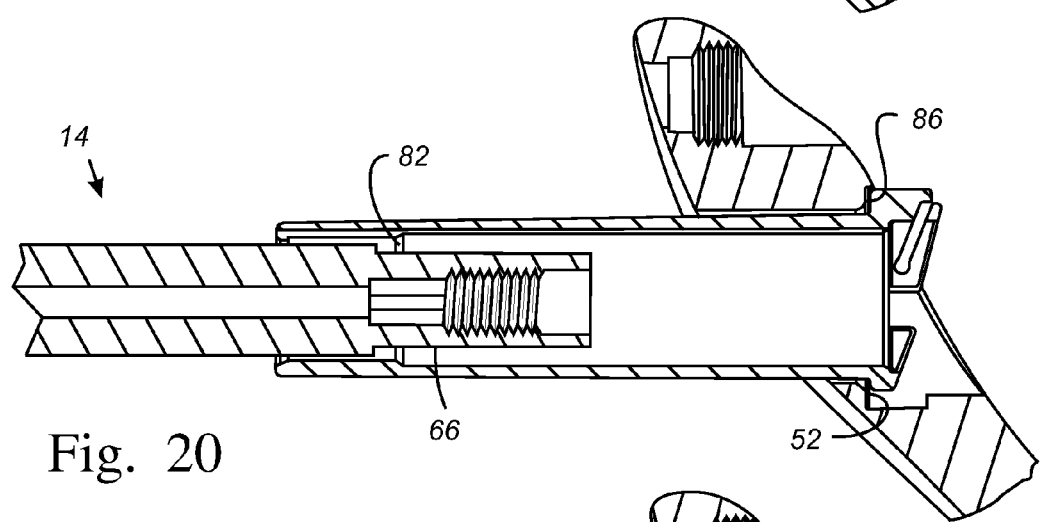
FIG. 20 depicts the barrel of the bone fixation assembly of FIG. 1 fully inserted within the side plate of FIG. 1.

In this example, however, the lag screw 14 has been positioned in approximately the desired position. Accordingly, movement of the barrel 16 into the hole 34 continues until the external ledge 86 contacts the internal ledge 52 of the hole 34 as shown in FIG. 20.

Figure 21:
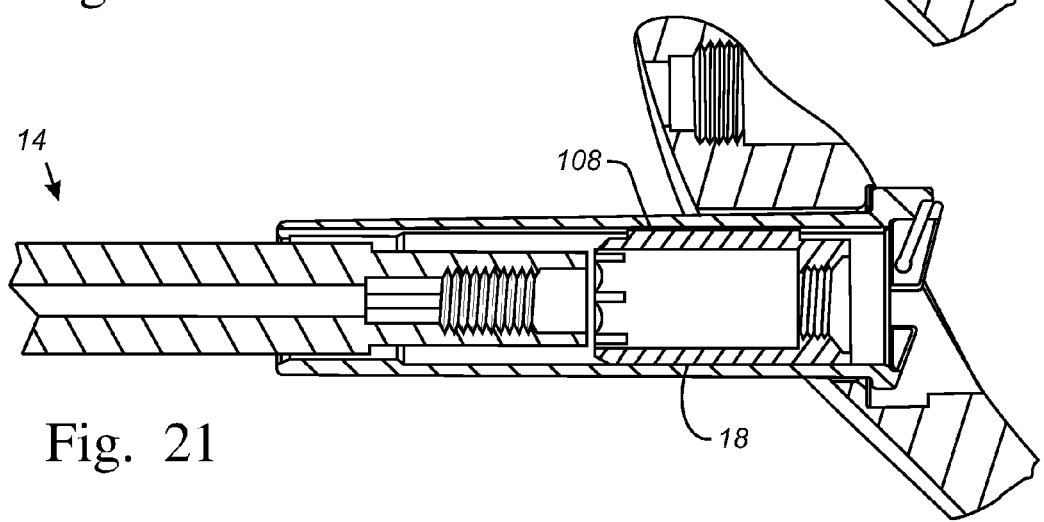
FIG. 21 depicts the sleeve of the bone fixation assembly of FIG. 1 inserted within the barrel of FIG. 1 with the key on the sleeve aligned with a slot in the barrel.

The next step in this example entails aligning the key 108 on the sleeve 18 with the slot 84 in the barrel 16. This allows the sleeve 18 to be inserted into the barrel 16 as shown in FIG. 21. Because the key 108 is within the slot 84, the sleeve 18 is angularly locked with respect to the barrel 16. In this example, the facets of internally faceted portion 112 of the sleeve 18 do not align with the external facets 74 of the upper portion 66 of the lag screw 14. Accordingly, the sleeve cannot be moved onto the lag screw 14. Rotation of the barrel 16 toward a locked position, in either a clockwise or a counter clockwise direction, will result in an alignment of the facets of internally faceted portion 112 of the sleeve 18 with the external facets 74 of the upper portion 66 of the lag screw 14 at some point prior to locking of the barrel 16 with the side plate 12. This is because the barrel 16 must be rotated one half turn (180 degrees) from the insertion position to the locking position while there are five external facets 74. Thus, each of the five facets spans an arc of seventy-two degrees. Accordingly, alignment of the facets of internally faceted portion 112 of the sleeve 18 with the external facets 74 necessarily occurs at a position less than one half turn (180 degrees) of rotation away from the insertion position of the barrel 16.

In an alternative arrangement, the lag screw 14 may be positioned within the hole 34 such that the facets of internally faceted portion 112 of the sleeve 18 align with the external facets 74 of the upper portion 66 of the lag screw 14 when the key 108 on the sleeve 18 is aligned with the slot 84 in the barrel 16. This is possible since the configuration of the internal facets 72 of the lag screw 14 is known. Thus, the insertion device used to insert the lag screw 14 may include one or more markings which, when aligned with a mark on the guide 36, results in the facets of internally faceted portion 112 of the sleeve 18 being aligned with the external facets 74 of the upper portion 66 of the lag screw 14 when the key 108 on the sleeve 18 is aligned with the slot 84 in the barrel 16.

In either approach, once the facets of internally faceted portion 112 of the sleeve 18 are aligned with the external facets 74 of the upper portion 66 of the lag screw 14, the sleeve 18 is inserted over the upper portion 66 of the lag screw 14 until the lower portion 106 of the sleeve 18 contacts the ledge 82 in the barrel 16. The barrel 16 is then rotated toward the locked position.

Rotation of the barrel 16 may be accomplished using a device such as the barrel insertion and removal tool 150 shown in FIGS. 22 and 23. The tool 150 includes a handle 152, a shaft 154 and a head 156. The shaft 154 is sized to fit slidingly within the hole 50 of the guide 36. The head includes two extensions 158 and 160 and a depressor 162. The extensions 158 and 160 are configured to engage the slots 102 and 104 of the barrel 16. Both the slots 102 and 104 and the extensions 158 and 160 are located less than ninety degrees apart. Therefore, there is only a single position at which the slots 102 and 104 and the extensions 158 and 160 will align. The tool 150 also includes an inner bore 164.

Figure 24:
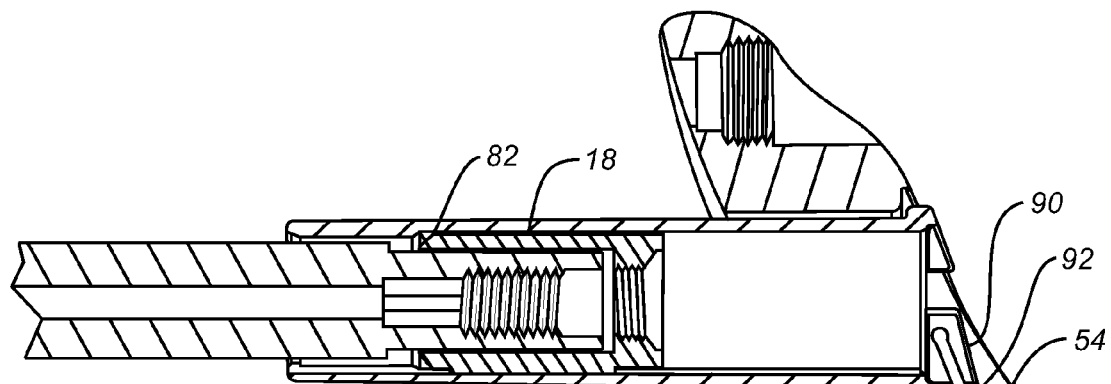
FIG. 24 depicts the barrel of the bone fixation assembly of FIG. 1 in a locked position within the side plate of FIG. 1.

Locking of the barrel 16 is effected by insertion of the extensions 158 and 160 into the slots 102 and 104 and rotation of the tool 150 in either a clockwise or a counterclockwise direction. When the extensions 158 and 160 are inserted into the slots 102 and 104, the depressor 162 will contact the mechanical spring 90. If desired, application of pressure to the handle 152 will cause the mechanical spring 90 to depress and the tool 150 may be rotated until the barrel 16 is in the locked position shown in FIG. 24.

Alternatively, the tool 150 may simply be rotated. Because the extensions 158 and 160 are longer than the depressor 162, the slots 102 and 104 may be engaged by the extensions 158 and 160 without the depressor 162 depressing the mechanical spring 90. In this approach, the rotation of the tool 150 causes one of the compressing portions 94 or 96 of the mechanical spring 90 to contact one of the compressing portions 58 or 56, respectively of the detent portion 54. Continued rotation causes the mechanical spring 90 to be compressed, allowing for further rotation. As the detent portion 92 is aligned with the retaining portion 60, the compressing force on the mechanical spring 90 is released and the mechanical spring 90 resumes its uncompressed state. Positive indication that a lock has been achieved is indicated by the movement of the mechanical spring 90.

In either event, when the barrel 16 is in the locked position, the substantially flat face of the detent portion 92 of the mechanical spring 90 is substantially aligned with the flat face of the retaining portion 60. Accordingly, rotation of the barrel 16 is not allowed until such time as the mechanical spring 90 is compressed and rotational force is applied to the barrel 18. Thus, the potential for accidental or undesired unlocking of the barrel 18 is reduced and the restriction of movement provides additional indication that an angular lock has been achieved.

Figure 25:
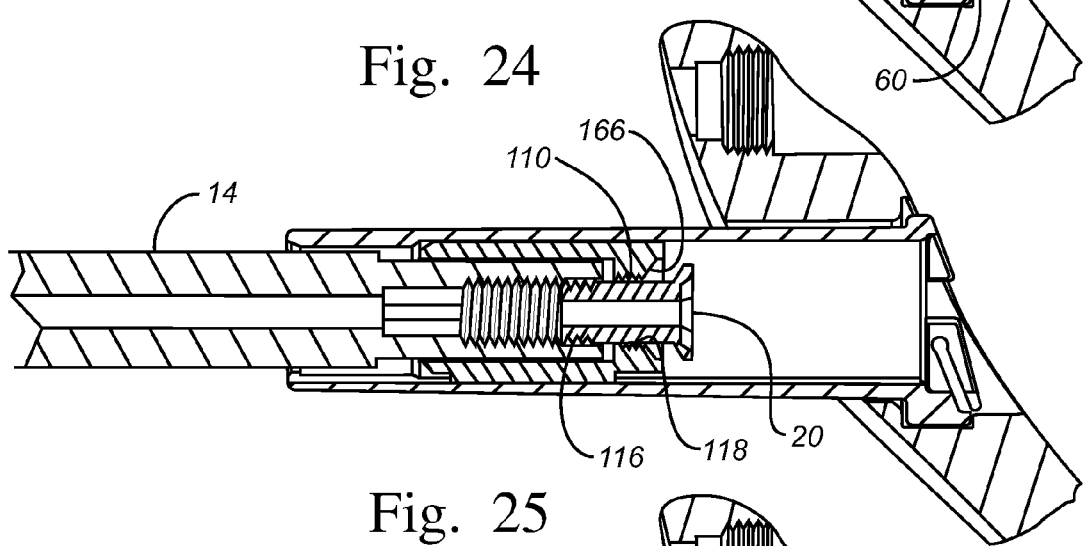
FIG. 25 depicts the lag screw retainer of FIG. 1 threaded through the sleeve of FIG. 1 with a portion of the faceted section of the lag screw outside of the sleeve.

Next, the lag screw retainer 20 is inserted into the hole 34 of the plate 12 and into the threaded portion 110 of the sleeve 18. Rotation of the lag screw retainer 20 causes the threaded portion 116 of the lag screw retainer 20 to be threaded past the threaded portion 110 of the of the sleeve 18 to the position shown in FIG. 25. As shown in FIG. 25, the neck portion 118 of the lag screw retainer 20 is longer and narrower than the threaded portion 110 of the sleeve 18. This allows the lag screw retainer 20 to be moved into the threaded section 70 of the lag screw 14.

Figure 26:
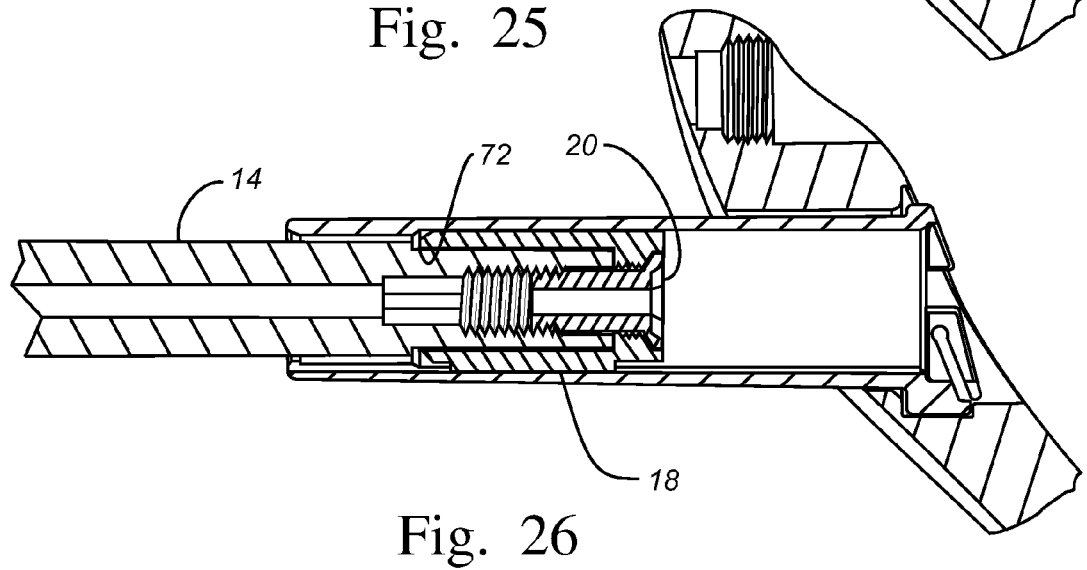
FIG. 26 depicts the lag screw retainer of FIG. 1 threaded into the lag screw of FIG. 1 with all of the faceted section of the lag screw inside of the sleeve.

The lag screw retainer 20 may be freely threaded into the threaded portion 70 of the lag screw 14 until the lag screw retainer 20 seats against the bevel portion 166 of the sleeve 18. The implant assembly is completed by rotating the lag screw retainer 20 clockwise until the unthreaded neck portion 118 is fully seated in the countersink 166 of the lag screw 14 as shown in FIG. 26.

Removal of the bone fixation assembly 10 is accomplished, generally, by reversing the above described sequence. The main difference, however, is that the mechanical spring 90 must be compressed to allow for rotation of the barrel 16 out of the locked position. Accordingly, once the extensions 158 and 160 as inserted into the slots 102 and 104, pressure is applied to the handle 152 causing the depressor 162 to depress the mechanical spring 90. Once the mechanical spring 90 is compressed, the barrel 16 may be rotated out of the locked position.

While the present invention has been illustrated by the description of exemplary processes and system components, and while the various processes and components have been described in considerable detail, applicant does not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept. By way of example, but not of limitation, the system described herein may be applied to other bones and joints besides the hip. Such bones may include tibial and humerus bones.

We claim:

1. A bone fixation assembly comprising:
a side plate configured to be mounted on a bone and having a hole therethrough, the hole including a first detent portion and an inner ledge, the first detent portion and the inner ledge protruding into the hole at different locations in the hole;
a barrel insertable into the hole and having a bore therethrough for placement of a portion of lag screw, the barrel including an upper portion having an external ledge and a second detent portion, the external ledge being a protrusion from the upper portion of the barrel that extends at least partially around a circumference of the upper portion of the barrel substantially perpendicular to the longitudinal axis of the barrel and configured for engagement with the inner ledge of the hole; and
a mechanical spring for biasing the second detent portion into a locking position with the first detent portion for angularly locking the barrel in relation to the side plate;
wherein the barrel further comprises a lower portion configured to pass through the hole prior to the upper portion, and
wherein the mechanical spring is located on the upper portion of the barrel such that when the barrel is inserted within the hole and the external ledge on the upper portion of the barrel is engaged with the inner ledge in the hole, rotation of the barrel from a first position to a second position forces the second detent portion against the first detent portion compressing the mechanical spring in a direction toward the lower portion of the barrel, and continued rotation of the barrel from the second position to a third position allows the mechanical spring to be released and bias the first detent portion in a direction away from the lower portion of the barrel into a position adjacent the first detent portion thereby angularly locking the barrel with the side plate.

2. The bone fixation assembly of claim 1, wherein the second detent portion is integrally formed with the mechanical spring and the mechanical spring is integrally formed with the barrel.

3. The bone fixation assembly of claim 1, wherein:
the side plate further comprises an inner side and an outer side, the hole extending between the inner side and the outer side, the inner side being configured for placement adjacent a bone, the outer side for placement opposite the bone;
the first detent portion is located between the inner ledge and the outer side; and
the barrel further comprises a lip on the upper portion configured such that when the barrel is angularly locked with the side plate, the lip is positioned adjacent to the first detent portion thereby restricting axial movement of the barrel.

4. The bone fixation assembly of claim 3, wherein the external ledge of the barrel includes a key complimentarily configured with the first detent portion such that alignment of the key with the first detent portion during insertion of the barrel into the hole enables the upper portion of the barrel to be slidably inserted into the hole such that the external ledge of the barrel contacts the inner ledge in the hole;

5. The bone fixation assembly of claim 1, wherein the bore of the barrel comprises an upper bore portion with a first diameter and a lower bore portion with a second diameter, the second diameter smaller than the first diameter, the assembly further comprising:
a lag screw with a first end portion and a threaded end portion, the first end portion sized to be positioned within the bore; and
a sleeve configured to engage the first portion of the lag screw and having a diameter greater than the second diameter and less than the first diameter such that the sleeve may be inserted into the upper bore portion so as to engage the lower bore portion.

6. The bone fixation assembly of claim 5, wherein:
the upper portion of the bore includes a key slot; and
the sleeve includes a key complimentary to the key slot, the combined diameter of the key and the sleeve larger than the first diameter but less than the combined diameter of the first diameter and the key slot such that when the key of the sleeve is aligned with the slot, the sleeve may be inserted into the upper bore portion.

7. The bone fixation assembly of claim 5, wherein:
the first end portion of the lag screw is internally threaded; and the sleeve includes an internal bore with a threaded upper portion and an unthreaded lower portion, the assembly further comprising:

a lag screw retainer having
- a threaded portion configured to be threaded though the threaded upper portion of the internal bore of the sleeve and into the internally threaded first end portion of the lag screw,
- a neck portion sized to extend though and beyond the threaded upper portion of the sleeve when the threaded portion of the lag screw retainer is threaded through the threaded upper portion of the internal bore of the sleeve and into the internally threaded first end portion of the lag screw, and
- a head portion having a diameter greater than the diameter of the threaded upper portion of the internal bore of the sleeve.

8. A method of assembling a bone fixation assembly comprising:

mounting a side plate having a hole therethrough on a bone, the side plate including a first detent portion having a first compressing portion and a first retaining portion;

inserting a lower portion of a barrel into the hole, the barrel being configured to receive a portion of a lag screw;

after the lower portion has been inserted into the hole, inserting an upper portion of the barrel into the hole, the upper portion of the barrel including a second detent portion and a mechanical spring operable to bias the second detent portion including a second compressing portion and a second retaining portion in a direction away from the lower portion of the barrel and toward a locked position;

rotating the barrel within the hole from a first position to a second position to cause the first compressing portion to contact the second compressing portion thereby compressing the mechanical spring toward the lower portion of the barrel to enable rotation of the barrel to a third position;

rotating the barrel from the second position to the third position to release the compression on the mechanical spring thereby angularly locking the barrel in relation to the side plate, wherein at the third position the mechanical spring is allowed to bias the second detent portion in the direction away from the lower portion of the barrel and into the locked position such that the second retaining portion is adjacent to the first retaining portion and rotation of the barrel with respect to the side plate is restricted.

9. The method of claim 8, wherein inserting a barrel comprises:

engaging a ledge in the hole with a ledge on the barrel.

10. The method of claim 9, wherein rotating the barrel from the second position to a third position further comprises:

positioning a lip adjacent to the second detent portion thereby restricting axial movement of the barrel.

11. The method of claim 10, wherein inserting a barrel comprises:

aligning a key of the ledge of the barrel with the second detent portion.

12. The method of claim 8, further comprising:

positioning an end portion of a lag screw within the barrel; and engaging the first end portion of the lag screw with a sleeve thereby angularly locking the sleeve and the lag screw.

13. The method of claim 12, further comprising:

aligning a key of the sleeve with a key slot in the barrel; and inserting the key into the barrel thereby angularly locking the sleeve and the barrel.

14. The method of claim 8, further comprising:

positioning the end portion of the lag screw within the barrel simultaneously with inserting the barrel into the hole.

15. A bone fixation assembly comprising:

a side plate for mounting on a bone, the side plate having a hole therethrough;

a barrel for receiving a portion of a lag screw, and configured to be inserted into the hole, the barrel including an upper portion and a lower portion, the lower portion being configured for insertion into the hole prior to the upper portion, the upper portion of the barrel including a first detent portion;

a mechanical spring located at the upper portion of the barrel and operable to bias the first detent portion including at least a first compressing portion and at least a first retaining portion in a direction away from the lower portion of the barrel and toward a locked position; and a second detent portion located on the side plate and including at least a second compressing portion and at least a second retaining portion, wherein rotation of the barrel within the hole from a first position to a second position causes the first compressing portion to contact the second compressing portion thereby compressing the mechanical spring in a direction toward the lower portion of the barrel so as to allow the barrel to be rotated to a third position wherein the mechanical spring is allowed to bias the first detent portion in the direction away from the lower portion of the barrel and into the locked position such that the first retaining portion is adjacent to the second retaining portion and rotation of the barrel with respect to the side plate is restricted.

16. The bone fixation assembly of claim 15, wherein:

the side plate further comprises an inner side and an outer side, the inner side being configured for placement adjacent a bone, the hole extending between the inner side and the outer side and including a ledge therein;

the second detent portion is located between the ledge and the outer side; and the barrel further comprises a lip on the upper portion configured such that when the barrel is angularly locked with the side plate, the lip is positioned adjacent to the second detent portion thereby restricting axial movement of the barrel.

17. The bone fixation assembly of claim 16, wherein the lip of the barrel comprises a key complimentarily configured with the first detent portion in the hole to allow the barrel to be inserted into the hole such that a ledge on the upper portion of the barrel contacts the ledge in the hole.

18. The bone fixation assembly of claim 15, wherein the barrel comprises an upper bore portion with a first diameter and a lower bore portion with a second diameter, the second diameter smaller than the first diameter, the assembly further comprising:

a lag screw with a first end portion and a threaded end portion, the first end portion sized to be positioned within the upper bore; and a sleeve with an inner bore configured to receive the first portion of the lag screw within the upper bore and having a diameter greater than the second diameter and less than the first diameter such that the sleeve may be inserted into the upper bore portion so as to engage the lower bore portion.

19. The bone fixation assembly of claim 18, wherein:

the upper bore portion includes a key slot; and the sleeve includes a key complimentary to the key slot, the combined diameter of the key and the sleeve larger than the first diameter but less than the combined diameter of the first diameter and the key slot such that when the key of the sleeve is aligned with the slot, the sleeve may be inserted into the upper bore portion.

* * * * *